United States Patent [19]

Farge et al.

[11] 4,153,698

[45] May 8, 1979

[54] ISOQUINOLINE DERIVATIVES AND PHARMACEUTICAL COMPOSITIONS CONTAINING THEM

[75] Inventors: Daniel Farge, Thiais; Alain Jossin, Saint Cloud; Gerard Ponsinet, Sucy-en-Brie; Daniel Reisdorf, Thiais, all of France

[73] Assignee: Rhone-Poulenc Industries, Paris, France

[21] Appl. No.: 871,136

[22] Filed: Jan. 20, 1978

[30] Foreign Application Priority Data

Jan. 20, 1977 [FR] France .................................. 77 01516
Dec. 23, 1977 [FR] France .................................. 77 39028

[51] Int. Cl.² .................... A61K 31/47; C07D 513/14
[52] U.S. Cl. ...................................... 424/258; 546/80
[58] Field of Search ...... 260/288 CF, 283 S, 283 CN; 424/258

[56] References Cited

U.S. PATENT DOCUMENTS 4,064,247  12/1977  Farge et al. .......................... 424/258

*Primary Examiner*—Donald G. Daus
*Assistant Examiner*—Diana G. Rivers
*Attorney, Agent, or Firm*—Stevens, Davis, Miller & Mosher

[57] ABSTRACT

Isoquinoline derivatives of the formula:

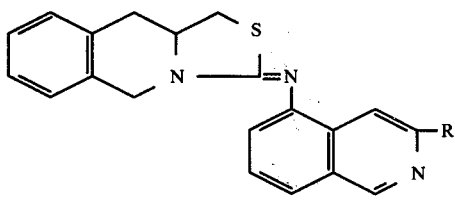

wherein R represents alkyl of 1 through 10 carbon atoms, which are new compounds, possess pharmacological properties and are particularly active as anti-inflammatory, analgesic and antipyretic agents.

8 Claims, No Drawings

ISOQUINOLINE DERIVATIVES AND PHARMACEUTICAL COMPOSITIONS CONTAINING THEM

This invention relates to new therapeutically useful isoquinoline derivatives, to processes for their preparation and to pharmaceutical compositions containing them.

The new isoquinoline derivatives of the present invention are those of the general formula:

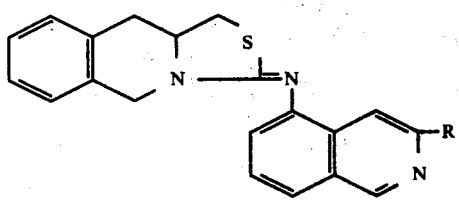

wherein R represents a straight- or branched-chain alkyl radical containing from 1 to 10 carbon atoms, and acid addition salts thereof.

The compounds of general formula I can exist in (R)— and (S)— forms and the invention includes both such forms and mixtures thereof.

According to a feature of the present invention the isoquinoline derivatives of general formula I are prepared by the process which comprises the reaction of a 5-aminoisoquinoline of the general formula:

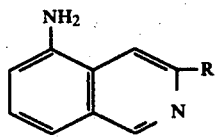

(wherein R is as hereinbefore defined) with a salt of the general formula:

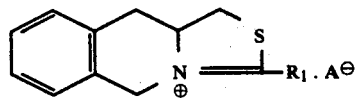

wherein $R_1$ represents a chlorine atom, an alkylthio radical containing from 1 to 4 carbon atoms (preferably methylthio) or a benzylthio radical, and $A^\ominus$ represents an anion such as a chloride, iodide, sulphate, tetrafluoroborate or fluorosulphonate ion.

When $R_1$ represents a chlorine atom, $A^\ominus$ represents a chloride ion. When $R_1$ represents an alkylthio or benzylthio radical, $A^\ominus$ represents an iodide, sulphate, tetrafluoroborate or fluorosulphonate ion.

When $R_1$ represents a chlorine atom and $A^\ominus$ represents a chloride ion, the reaction is preferably carried out in an organic solvent, such as acetonitrile, in the presence of a base, such as triethylamine, at a temperature of about 20° C.

When $R_1$ represents an alkylthio or benzylthio radical and $A^\ominus$ represents an iodide, sulphate, tetrafluoroborate or fluorosulphonate ion, the reaction is preferably carried out in a basic organic solvent, such as pyridine, at a temperature of about 20° C.

The salt of general formula III wherein $R_1$ represents a chlorine atom and $A^\ominus$ represents a chloride ion can be obtained by the reaction of a chlorinating agent, such as phosgene, phosphorus pentachloride, thionyl chloride or oxalyl chloride, on 1,5,10,10a-tetrahydrothiazolo[3,4-b]isoquinoline-3-thione of the formula:

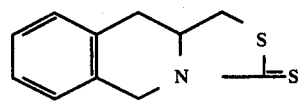

The reaction is generally carried out in an organic solvent or in a mixture of organic solvents, such as a mixture of toluene and tetrahydrofuran, at a temperature of from 0° to 70° C.

The salts of general formula III wherein $R_1$ represents an alkylthio or benzylthio radical and $A^\ominus$ represents an iodide, sulphate, tetrafluoroborate or fluorosulphonate ion, can be obtained by the reaction of a reactive ester of the general formula:

$$R_2 - A_1 \qquad\qquad V$$

(wherein $R_2$ represents an alkyl radical containing 1 to 4 carbon atoms or a benzyl radical, and $A_1$ represents the residue of a reactive ester such as an iodine atom or an alkoxysulphonyloxy radical), or of triethyloxonium tetrafluoroborate or methyl fluorosulphonate, with a compound of general formula IV. The reaction is generally effected, optionally in the presence of an organic solvent such as methylene chloride, at a temperature of about 20° C.

The thiazoloisoquinoline derivatives of formula IV can be obtained by the reaction of carbon disulphide, in a basic medium, with a 1,2,3,4-tetrahydroisoquinoline of the general formula:

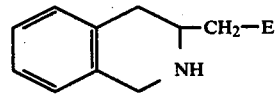

wherein E represents a halogen, e.g. bromine or chlorine, atom or a hydroxysulphonyloxy radical. The reaction is generally carried out in an aqueous medium in the presence of sodium hydroxide at a temperature of about 20° C.

Compounds of general formula VI can be obtained by the action of an inorganic acid on 3-hydroxymethyl-1,2,3,4-tetrahydroisoquinoline of the formula:

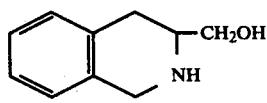

the preparation of which is mentioned hereafter.

The compound of general formula VI wherein E represents the hydroxysulphonyloxy radical is generally prepared by treatment of 3-hydroxymethyl-1,2,3,4-tetrahydroisoquinoline with sulphuric acid in an aqueous medium at a temperature of about 100° C., or in an organic solvent (such as dimethylformamide) in the presence of dicyclohexylcarbodiimide at a temperature of about 20° C.

The compound of general formula VI wherein E represents the bromine atom is generally prepared by treatment of the said 3-hydroxymethyl compound with aqueous hydrobromic acid (48% w/v), at the reflux temperature of the reaction mixture, and isolating the product of general formula VI as its hydrobromide.

The compound of general formula VI wherein E represents the chlorine atom is generally prepared by treatment of the said 3-hydroxymethyl compound with thionyl chloride, in an organic solvent, such as chloroform saturated with hydrogen chloride gas, at the reflux temperature of the reaction mixture, and isolating the product of general formula VI as its hydrochloride.

3-Hydroxymethyl-1,2,3,4-tetrahydroisoquinoline can be prepared from phenylalanine in accordance with the method described by S. Yamada and T. Kunieda, Chem. Pharm. Bull., 15, 490, (1967).

When L-phenylalanine is used, the product of general formula I ultimately obtained is in the (S) form.

When D-phenylalanine is used, the product of general formula I ultimately obtained is in the (R) form.

When D,L-phenylalanine is used, the product of general formula I ultimately obtained is in the (R,S) form.

The 5-aminoisoquinolines of general formula II can be obtained from 3-alkylisoquinolines of the general formula:

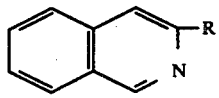

VIII (wherein R is as hereinbefore defined) by application of the method described by N. P. Buu-Hoï et al., J. Chem. Soc., 3,924, (1964).

The 3-alkylisoquinolines of general formula VIII can be obtained in accordance with the method described by J. Murakoshi et al., Yakugaku Zasshi, 79, 1,578, (1959), or in accordance with the method described by F. Damerow, Ber., 27, 2,232, (1894).

According to a further feature of the present invention, the isoquinoline derivatives of general formula I are prepared by the process which comprises the cyclisation of a 1,2,3,4-tetrahydroisoquinoline of the general formula:

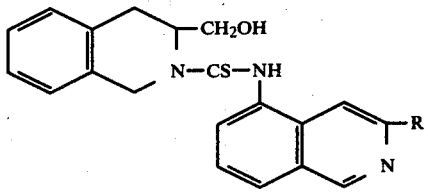

IX wherein R is as hereinbefore defined. The cyclisation reaction is generally carried out by heating the compound of formula IX in an acid medium. It is particularly advantageous to effect the cyclisation at a temperature between 65° and 100° C. in an aqueous solution of an inorganic acid, for example in hydrochloric acid.

The 1,2,3,4-tetrahydroisoquinolines of general formula IX can be obtained by the reaction of an isothiocyanate of the general formula:

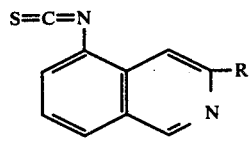

X (wherein R is as hereinbefore defined) with 3-hydroxymethyl-1,2,3,4-tetrahydroisoquinoline (prepared as mentioned heretofore). Generally the reaction is carried out in an organic solvent such as an alcohol, for example ethanol, operating at a temperature between 20° and 50° C.

The isothiocyanates of general formula X can be obtained by the reaction of carbon disulphide with a 5-aminoisoquinoline of general formula II, followed by the addition of dicyclohexylcarbodiimide. The reaction is generally carried out in the presence of a base such as a tertiary amine, for example triethylamine. Advantageously it is effected in an organic solvent, such as pyridine at a temperature between −10° and 25° C.

The isoquinoline derivatives of general formula I may be converted by known methods into acid addition salts. The acid addition salts may be obtained by the action of acids on the isoquinoline derivatives in appropriate solvents. As organic solvents there may be used alcohols, ketones, ethers or chlorinated hydrocarbons. The salt which is formed is precipitated, if necessary after concentrating the solution, and is isolated by filtration or by decantation.

The isoquinoline derivatives of general formula I and/or their acid addition salts can optionally be purified by physical methods such as crystallisation or chromatography.

The isoquinoline derivatives of general formula I and their acid addition salts possess useful pharmacological properties. They are particularly active as anti-inflammatory, analgesic and antipyretic agents.

The anti-inflammatory activity is demonstrated in rats at doses of between 5 and 80 mg/kg administered orally, in accordance with the technique of K. F. Benitz and L. M. Hall [Arch. Int. Pharmacodyn., 144, 185, (1963)].

The analgesic activity is demonstrated in rats at doses of between 2.5 and 50 mg/kg administered orally, when using the technique of E. Siegmund et al., Proc. Soc. Exp. Biol. Med., 95, 729, (1957) and the technique of L. O. Randall and J. J. Selitto, Arch. Int. Pharmacodyn., 111, 409, (1957), modified by K. F. Swingle et al., Proc. Soc. Exp. Biol. Med., 137, 536, (1971).

The antipyretic activity is demonstrated in rats at doses of between 1.5 and 25 mg/kg administered orally, when using the technique of J. J. Loux et al., Toxicol. Appl. Pharmacol., 22, 674, (1972).

The toxicity in mice of the compounds according to the invention is greater than 300 mg/kg administered orally, and most of the compounds show no sign of toxicity in mice at a dose of 900 mg/kg administered orally.

For therapeutic purposes, the isoquinoline derivatives of general formula I may be employed as such or in the form of pharmaceutically acceptable acid addition salts, that is to say salts which are non-toxic at the doses used for therapy. Suitable acid addition salts are hydrochlorides, sulphates, nitrates, phosphate, acetates, propionates, succinates, benzoates, fumarates, maleates, tartrates, theophyllinacetates, salicylates, phenolphthalinates and methylene-bis-β-hydroxynaphthoates.

The isoquinoline derivatives of general formula I wherein R represents a straight- or branched-chain alkyl radical containing 1 to 5 carbon atoms are of particular value, and especially those wherein R represents a straight-chain alkyl radical containing 1 to 4 carbon atoms which are the most active.

The following non-limitative Examples illustrate the preparation of isoquinoline derivatives of the present invention.

EXAMPLE 1

(S)-3-Methylthio-1,5,10,10a-tetrahydrothiazolo-[3,4-b]isoquinolinium iodide (36.3 g) is added to a solution of 5-amino-3-methylisoquinoline (15.9 g) in pyridine (200 cc). The suspension obtained gradually goes into solution. After 24 hours at a temperature of about 20° C., the mixture is concentrated to dryness under reduced pressure (25 mm Hg) at 50° C. The residue is dissolved in a mixture of methylene chloride (600 cc) and N aqueous sodium hydroxide solution (400 cc). The organic phase is decanted, washed with water (200 cc), dried over magnesium sulphate, filtered and the filtrate is then concentrated to dryness under reduced pressure (40 mm Hg) at 40° C. The residue obtained is recrystallised from acetonitrile (500 cc). (S)-3-[(3-Methylisoquinol-5-yl)imino]-1,5,10,10a-tetrahydrothiazolo-[3,4-b]isoquinoline (29.2 g), which melts at 181° C., is thus obtained.

$[\alpha]_D^{20} = -180° \pm 2°$ (c=1, chloroform).

(S)-3-Methylthio-1,5,10,10a-tetrahydrothiazolo-[3,4-b]isoquinolinium iodide can be prepared in the following manner:

(S)-1,5,10,10a-Tetrahydrothiazolo[3,4-b]isoquinoline-3-thione (38 g) is dissolved in methyl iodide (500 cc). After 15 hours at a temperature of about 20° C., the resulting crystals are filtered off, washed with diethyl ether (2×50 cc) and then dried at 20° C. under reduced pressure (1 mm Hg). (S)-3-Methylthio-1,5,10,10a-tetrahydrothiazolo[3,4-b]isoquinolinium iodide (61.5 g), which melts at 140°-150° C. with decomposition, is thus obtained.

(S)-1,5,10,10a-Tetrahydrothiazolo[3,4-b]isoquinoline-3-thione can be prepared in the following manner:

Carbon disulphide (40 g) is added dropwise, whilst stirring vigorously, to a solution of (S)-3-hydroxysulphonyloxymethyl-1,2,3,4-tetrahydroisoquinoline (100 g) in 0.25 N aqueous sodium hydroxide solution (4000 cc). The reaction is exothermic. A solid precipitates; the stirring is continued for 3 hours. The reaction mixture is then neutralised by the addition of 4 N hydrochloric acid. The resulting crystals are filtered off, washed copiously with water and then recrystallized from ethanol (3000 cc). (S)-1,5,10,10a-Tetrahydrothiazolo[3,4-b]isoquinoline-3-thione (77 g) is thus obtained in the form of fine white needles which melt at 150° C.

$[\alpha]_D^{20} = -377° \pm 4°$ (c=1, chloroform).

(S)-3-Hydroxysulphonyloxymethyl-1,2,3,4-tetrahydroisoquinoline can be prepared in the following manner:

A solution of (S)-3-hydroxymethyl-1,2,3,4-tetrahydroisoquinoline (41 g) in a mixture of 34 N sulphuric acid (13 cc) and water (70 cc) is heated at 110° C. Water (about 50 cc) is distilled off and the residue is then concentrated at 100° C. under reduced pressure (20 mm Hg). The brown oily residue is taken up in a mixture of 34 N sulphuric acid (13 cc) and water (70 cc). Water (50 cc) is again distilled off, the mixture is then concentrated as described above, and the concentration process is concluded at 100° C. under reduced pressure (1 mm Hg). The residue, which crystallises on cooling, is recrystallised from a mixture of ethanol (140 cc) and water (60 cc). After cooling for 15 hours at about 5° C., the resulting crystals are filtered off and washed with a mixture (20 cc) of ethanol and water (3-1 by volume) and then with ethanol (2×25 cc). After drying at 60° C. under reduced pressure (1 mm Hg), (S)-3-hydroxysulphonyloxymethyl-1,2,3,4-tetrahydroisoquinoline (48 g) is obtained in the form of white crystals.

$[\alpha]_D^{20} = -55° \pm 1°$ (c=1, dimethyl sulphoxide).

(S)-3-Hydroxymethyl-1,2,3,4-tetrahydroisoquinoline can be prepared from L-phenylalanine in accordance with the method described by S. Yamada and T. Kunieda, Chem. Pharm. Bull., 15, 490, (1967).

EXAMPLE 2

By following the procedure of Example 1 but using 5-amino-3-methylisoquinoline (15.9 g) and (RS)-3-methylthio-1,5,10,10a-tetrahydrothiazolo[3,4-b]isoquinolinium iodide (36.3 g) as starting materials, (RS)-3-[(3-methylisoquinol-5-yl)imino]-1,5,10,10a-tetrahydrothiazolo[3,4-b]isoquinoline (27.8 g), which melts at 159° C., is obtained.

(RS)-3-Methylthio-1,5,10,10a-tetrahydrothiazolo-[3,4-b]isoquinolinium iodide can be prepared in the following manner:

(RS)-1,5,10,10a-Tetrahydrothiazolo[3,4-b]isoquinoline-3-thione (210 g) is dissolved in methylene chloride (4000 cc), whilst warming to 30° C. Methyl iodide (202 g) is run in over a period of fifteen minutes, and the mixture is then stirred for 64 hours at a temperature of about 20° C. The resulting crystals are filtered off and washed with diethyl ether. After drying under reduced pressure (1 mm Hg), (RS)-3-methylthio-1,5,10,10a-tetrahydrothiazolo[3,4-b]isoquinolinium iodide (221.7 g), which melts at about 180° C. with decomposition, is obtained.

(RS)-1,5,10,10a-Tetrahydrothiazolo[3,4-b]isoquinoline-3-thione can be prepared in the following manner:

Carbon disulphide (63 g) is added dropwise, at 20° C. and whilst stirring vigorously, to a solution of (RS)-3-hydroxysulphonyloxymethyl-1,2,3,4-tetrahydroisoquinoline (151 g) and sodium hydroxide pellets (63 g) in water (5000 cc). A cream precipitate is immediately formed. The very thick mixture is stirred at a temperature of about 20° C. for 24 hours. The reaction mixture is then neutralised by adding 4 N hydrochloric acid (130 cc). The solid is filtered off and then washed copiously with water. After drying, (RS)-1,5,10,10a-tetrahydrothiazolo[3,4-b]isoquinoline-3-thione (107 g) is obtained in the form of white crystals which melt at 180° C.

(RS)-3-Hydroxysulphonyloxymethyl-1,2,3,4-tetahydroisoquinoline can be prepared in the following manner:

34 N Sulphuric acid (d=1.83; 36.8 cc) is added, over a period of a few minutes, to a suspension of (RS)-3-hydroxymethyl-1,2,3,4-tetrahydroisoquinoline (106 g) in water (226 cc). The temperature rises to 60° C. and the solid goes into solution. The mixture is heated at 100°-110° C. whilst water is distilled off, and then at 160° C. whilst concentrating under reduced pressure (20 mm Hg). The concentration process is concluded under a pressure of 1mm Hg. The residue crystallises on cooling. Crude (RS)-3-hydroxysulphonyloxymethyl-1,2,3,4-tetrahydroisoquinoline (151 g) is thus obtained in the form of pale yellow crystals.

(RS)-3-Hydroxymethyl-1,2,3,4-tetrahydroisoquinoline can be prepared in accordance with the method of S. Yamada and T. Kunieda, Chem. Pharm. Bull. 15, 490, (1967).

EXAMPLE 3

(S)-3-Methylthio-1,5,10,10a-tetrahydrothiazolo-[3,4-b]isoquinolinium iodide (5.25 g) is added to a solution of 5-amino-3-butylisoquinoline (3 g) in pyridine (100 cc). The suspension obtained dissolves gradually. After 4 days at a temperature of about 20° C., the mixture is concentrated to dryness under reduced pressure (25 mm Hg) at 50° C. The residue is dissolved in chloroform (200 cc). This solution is washed with N aqueous sodium hydroxide solution (3×100 cc) and then with water (2×50 cc), dried over sodium sulphate, filtered and the filtrate is then concentrated to dryness under reduced pressure (40 mm Hg) at 40° C. The residue obtained is recrystallised from diisopropyl ether (50 cc). (S)-3-[(3-Butylisoquinol-5-yl)imino]-1,5,10,10a-tetrahydrothiazolo[3,4-b]-isoquinoline (3.05 g), which melts at 82° C., is thus obtained.

$[\alpha]_D^{20} = -156° \pm 2°$ (c=1, chloroform).

5-Amino-3-butylisoquinoline can be prepared by applying the method of N. P. Buu-Hoï et al., J. Chem. Soc., 3,924, (1964).

EXAMPLE 4

By following the procedure of Example 3 but using 5-amino-3-ethylisoquinoline (7.1 g) and (S)-3-methylthio-1,5,10,10a-tetrahydrothiazolo[3,4-b]isoquinolinium iodide (13.7 g) as starting materials, (S)-3-[(3-ethylisoquinol-5-yl)imino]-1,5,10,10a-tetrahydrothiazolo[3,4-b]isoquinoline (8.6 g), which melts at 142° C. after recrystallisation from ethanol, is obtained.

$[\alpha]_D^{20} = -162° \pm 2°$ (c=1, chloroform).

5-Amino-3-ethylisoquinoline can be prepared by applying the method of N. P. Buu-Hoï, J. Chem. Soc., 3,924, (1964).

EXAMPLE 5

By following the procedure of Example 3 but using 5-amino-3-propylisoquinoline (0.18 g) and (S)-3-methylthio-1,5,10,10a-tetrahydrothiazolo[3,4-b]isoquinolinium iodide (0.35 g) as starting materials, (S)-3-[(3-propylisoquinol-5-yl)imino]-1,5,10,10a-tetrahydrothiazolo[3,4-b]isoquinoline (0.35 g) is obtained in a crude form, which is purified by chromatography on a column (diameter of the column: 0.7 cm) containing silica (6 g) by eluting with methylene chloride and collecting the eluate in 20 cc fractions.

Fractions 7 to 11 are evaporated, and (S)-3-[(3-propylisoquinol-5-yl)imino]-1,5,10,10a-tetrahydrothiazolo-[3,4-b]isoquinoline (0.21 g) is thus obtained in the form of pale yellow crystals which, after recrystallisation from diisopropyl ether, melt at 95°-96° C.

$[\alpha]_D^{20} = -145.5° \pm 1°$ (c=1, chloroform).

The present invention includes within its scope pharmaceutical compositions comprising, as active ingredient, at least one of the compounds of general formula I, or a non-toxic acid addition salts thereof, in association with a pharmaceutical carrier or coating. The invention includes especially such preparations made up for oral, parenteral, rectal or local administration.

Solid compositions for oral administration include tablets, pills, powders and granules. In such solid compositions the active compound is admixed with at least one inert diluent such as sucrose, lactose or starch. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as liquid paraffin. Besides inert diluents such compositions may also comprise adjuvants, such as wetting, emulsifying and suspending agents, and sweetening, flavouring and aromatizing agents. The compositions according to the invention, for oral administration also include capsules of absorbable material such as gelatin containing the active substance with or without the addition of diluents or excipients.

Preparations according to the invention for parenteral administration include sterile non-aqueous solutions, suspensions or emulsions. Examples of non-aqueous solvents or vehicles are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilized by, for example, filtration through a bacteria-retaining filter, by incorporation in the compositions of sterilizing agents, by irradiation, or by heating. They may also be manufactured in the form of sterile solid compositions which can be dissolved in a sterile injectable medium immediately before use.

Compositions for rectal administration are suppositories which contain, in addition to the active substance, excipients such as cacao butter or a suitable wax base.

Compositions for local administration can be, for example, in the form of ointments.

The percentage of active ingredient in the compositions of the invention may be varied, it being necessary that it should constitute a proportion such that a suitable dosage shall be obtained.

The compositions according to the invention are particularly useful in human therapy by virtue of their anti-inflammatory, analgesic and antipyretic effects. They are particularly suitable for the treatment of inflammatory diseases (ankylosing spondylarthritis, acute articular rheumatism and arthrosis), acute and chronic pains, rheumatic and traumatic algias, dental, neurological and visceral pains, various algias (pains experienced by cancer patients), febrile conditions, and medical, surgical and obstetrical complaints giving rise to thrombosis and embolisms. In human therapy, the doses depend on the desired effect and on the duration of the treatment; they are generally between 150 and 2000 mg per day for an adult.

In general terms, the physician will decide the posology which he considers to be most appropriate, taking into account the age, weight and any other factors intrinsic to the patient being treated.

The following Examples illustrate pharmaceutical compositions according to the invention.

EXAMPLE 6

Tablets containing the active product (100 mg) and having the following composition are prepared in accordance with the usual technique:

| | |
|---|---|
| (S)-3-[(3-methylisoquinol-5-yl)imino]-1,5,10,10a-tetrahydrothiazolo[3,4-b]isoquinoline | 0.100 g |
| starch | 0.110 g |
| precipitated silica | 0.035 g |
| magnesium stearate | 0.005 g |

EXAMPLE 7

Tablets containing the active product (100 mg) and having the following composition are prepared in accordance with the usual technique:

| | |
|---|---|
| (S)-3-[(3-ethylisoquinol-5-yl)imino]-1,5,10,10a-tetrahydrothiazolo[3,4-b]isoquinoline | 0.100 g |
| starch | 0.110 g |
| precipitated silica | 0.035 g |
| magnesium stearate | 0.005 g |

We claim:

1. An isoquinoline derivative of the formula:

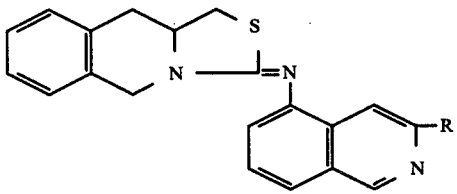

wherein R represents alkyl of 1 through 10 carbon atoms, and non-toxic pharmaceutically acceptable acid addition salts thereof.

2. An isoquinoline derivative according to claim 1 wherein R represents alkyl of 1 through 5 carbon atoms, and non-toxic pharmaceutically acceptable acid addition salts thereof.

3. An isoquinoline derivative according to claim 1 wherein R represents a straight-chain alkyl radical of 1 through 4 carbon atoms, and non-toxic pharmaceutically acceptable acid addition salts thereof.

4. An isoquinoline derivative according to claim 1 which is 3-[(3-methylisoquinol-5-yl)imino]-1,5,10,10a-tetrahydrothiazolo[3,4-b]isoquinoline and its non-toxic pharmaceutically acceptable acid addition salts.

5. An isoquinoline derivative according to claim 1 which is 3-[(3-butylisoquinol-5-yl)imino]-1,5,10,10a-tetrahydrothiazolo[3,4-b]isoquinoline and its non-toxic pharmaceutically acceptable acid addition salts.

6. An isoquinoline derivative according to claim 1 which is 3-[(3-ethylisoquinol-5-yl)imino]-1,5,10,10a-tetrahydrothiazolo[3,4-b]isoquinoline and its non-toxic pharmaceutically acceptable acid addition salts.

7. An isoquinoline derivative according to claim 1 which is 3-[(3-propylisoquinol-5-yl)imino]-1,5,10,10a-tetrahydrothiazolo[3,4-b]isoquinoline and its non-toxic pharmaceutically acceptable acid addition salts.

8. A pharmaceutical composition useful as an analgesic, anti-pyretic or anti-inflammatory which comprises as active ingredient an effective amount of an isoquinoline derivative as claimed in claim 1, or a non-toxic pharmaceutically acceptable acid addition salt thereof, in association with a significant amount of a pharmaceutical carrier.

* * * * *